United States Patent [19]

Shah

[11] Patent Number: 5,814,329

[45] Date of Patent: Sep. 29, 1998

[54] HYDROPHILIC POLYSTYRENE GRAFT COPOLYMER VEHICLE FOR INTRAVAGINAL ADMINISTRATION OF PHARMACOLOGICALLY ACTIVE AGENTS

[75] Inventor: Kishore R. Shah, Bridgewater, N.J.

[73] Assignee: Polytherapeutics, Inc., Bridgewater, N.J.

[21] Appl. No.: 746,327

[22] Filed: Nov. 12, 1996

[51] Int. Cl.⁶ .............................. A61K 47/32; A61K 9/02
[52] U.S. Cl. ......................... 424/433; 424/430; 514/967
[58] Field of Search ................................ 424/772.1, 430, 424/433; 514/967

[56] References Cited

U.S. PATENT DOCUMENTS

| | | | |
|---|---|---|---|
| 4,085,168 | 4/1978 | Milkovich et al. | 260/886 |
| 4,693,887 | 9/1987 | Shah | 424/486 |
| 5,425,955 | 6/1995 | Narayanan et al. | 424/405 |
| 5,429,826 | 7/1995 | Nair et al. | 514/772.1 |
| 5,474,768 | 12/1995 | Nair et al. | 574/772.1 |
| 5,536,743 | 7/1996 | Borgman | 514/967 |

*Primary Examiner*—Peter F. Kulkosky

[57] ABSTRACT

This invention pertains to the vaginal delivery of pharmacologically active agents and to polymeric formulations that allow for a prolonged release of the active agents in the vaginal environment. More specically the invention pertains to compositions for the delivery of drugs intravaginally comprising a drug or a plurality of drugs to be delivered and a thermoplastic graft copolymer, said graft copolymer being the reaction product of a polystyrene macromonomer having an ethylenically unsaturated functional group and at least one hydrophilic monomer having an ethylenically unsaturated functional group.

32 Claims, No Drawings

HYDROPHILIC POLYSTYRENE GRAFT COPOLYMER VEHICLE FOR INTRAVAGINAL ADMINISTRATION OF PHARMACOLOGICALLY ACTIVE AGENTS

FIELD OF THE INVENTION

This invention pertains to the vaginal delivery of pharmacologically active agents and more specifically to polymeric formulations that allow for a prolonged release of the active agents in the vaginal environment.

BACKGROUND OF THE INVENTION

The average female human vagina is approximately 7 cm in length and 2 cm wide with many folds to increase its surface area. It can hold as much as 3 gms of fluid without leakage. The pH of the vagina is about 4. After menopause the vagina shrinks about 25% in both length and width and the pH increases to about 7.

Present day drug delivery to the human vagina is limited by the residence time in it and the ability of the delivery system to contain and release in a controlled manner both hydrophilic and hydrophobic drugs. Typical systems such as foams, gels, and tablets are removed by the self cleansing action of the vaginal track. In addition, these systems do not have the capability or flexibility to release different types of drugs in a controlled release mode. It is, therefore, one direct object of the present invention to provide a polymeric formulation that stays in the vaginal cavity for an extended period of time, and which also has the flexibility of delivering both hydrophilic as well as hydrophobic drugs in a controlled manner.

There are several advantages of using vaginal delivery of drugs as opposed to taking oral pills. For indications that require the treatment drug in the vaginal tissues, e.g. estradiol to saturate the estrogen receptors, the vaginal drug administration provides a site specific drug delivery with minimal systemic dilution of the drug. Thus, substantially smaller doses of the drug will be needed. In addition, the side effects of systemic drug circulation will be minimized.

The oral medication doses for estrogen to minimize the symptons of the postmenopausal syndrome are 500, 1000, and 2000 micrograms per day although the requirement is only 50 micrograms, substantiated from clinical investigations of its delivery by a transdermal mode. Estradiol as well as estriol are also used in vaginal creams to replenish the vaginal moisture and improve the tissue resiliency of postmenopausal women. The concentration of estradiol in the commercial vaginal creams is only 0.01% (1995 Physicians GenRx, Mosby Yearbook Inc., St. Louis, p.II 743).

Menopause in women is associated with many troublesome side effects such as hot flashes, vaginal dryness, mood swings, and lowered libido. With rapid increase in use of estrogen to alleviate the above mentioned symptoms, the use of progestins is also increasing. Ten to fourteen days of progesterone delivery is needed when estradiol is administered, to protect the womb from cancer, i.e. to transform the endometrium from proliferative to secretory.

Progesterone as well as medroxyprogesterone acetate are available in oral dosage form or as suspensions for intramuscular injection (1995 Physicians GenRx, Mosby Yearbook, Inc., St. Louis, p.II 1227 and p.II 1655). The administration of progestin by methods described above causes bloating, weight gain, headaches, depression and other undesirable side effects. Oral progesterone is only 5% bioavailable due to hepatic first pass metabolism with the resultant metabolites causing central nervous system and liver toxicity. Although vaginal cream dosage form of progesterone has not been approved by the FDA, most hospital pharmacies prepare such creams, which can also be purchased from Professional Technical Services or Health Directions [Health Wisdom for Women, Phillips Publishing Co., Potomac, Md., p. 2 (1996)]. These progesterone creams are used thrice a week for two weeks every month after the menstrual period.

Thus, another object of this invention is to minimize side effects by delivering drugs site specifically(vaginal).

Attempts have been made to improve the residence time of the delivery system in the vagina by the use of bioadhesive gels. Lightly crosslinked polyacrylic acid has been used as a mucoadhesive gel and it is claimed to remain in the vaginal cavity for 2 to 3 days. It is further claimed that, because of its polyelectrolytic nature, it reduces the pH of the vaginal tissue from 7 to 4 in postmenopausal women. The reduction in pH is significant because it provides an unfavorable environment for growth of yeast and bacteria. Bacterial vaginosis in postmenopausal women is due to the change in the pH and the replacement of normal flora with one that flourishes under more basic conditions. Metronidazole and other broad spectrum antibacterials can be used to treat bacterial vaginosis but the pH has to be reduced to eliminate recurrence. Polyacrylic acid is also claimed to reduce vaginal dryness associated with postmenopause due to the reduction in circulating estrogen causing itchiness and pain and bleeding during intercourse.

Although mucoadhesive gels are improvements over the prior art of plain gels and ointments, they do not adhere to the vaginal tissue for an extended period of time. Furthermore, these gels are not flexible enough to allow for the incorporation of both hydrophobic amd hydrophilic drugs and the delivery of these drugs in a controlled way. Polyacrylic acid absorbs 100% of its weight in water and it will quickly dump any drug incorporated in it. It is, therefore, part of this invention to provide a polymeric formulation that will reduce vaginal dryness and reduce the pH of the vaginal tissue for at least 3.5 days and optimally up to 7+ days. It is also another object of this invention to provide a gel for adhesion to the vaginal tissue and provide the capability to deliver drugs in a prolonged and controlled way.

Other drugs that may be advantageously delivered to the vaginal cavity include spermicidals and antivirals to prevent conception and sexually transmitted diseases. A marketed product, Today sponge, contains one gram of nonoxynol-9, spermicide which is applied 10 minutes prior to intercourse. It is another object of the present invention to allow for the delivery of smaller but effective amounts of spermicides and antiviral compounds at least several hours prior to sexual intercourse.

The vaginal port has been used extensively to deliver drugs to the vaginal area for local or systemic therapeutic effect by bypassing the hepatic first pass metabolism. Some of these examples are described below:

Acyclopirox, an antimycotic with activity against yeast as well as gram positive and gram negative bacteria was delivered as a vaginal cream preparation [J. of Chemotherapy,Vol. 5, No. 5, p307 (1993)]. Propranolol, a cardiovascular beta blocker was delivered as a vaginal cream and it was shown to be an inhibitor of sperm motility [Xenobiotica, Vol. 19, p883 (1989)]. Sulfanilamide cream, betadine vaginal gel, condeptin vaginal ointment, chlotrimazole vaginal tablets, micanozole vaginal cream, nystatin vaginal cream, chlordantoin vaginal cream, and tricandil vaginal candelettes were tested and compared against each other for antifungal activity [Postgraduate Medical Journal, Vol. 55, p648 (1979)]. Delivery of progestational steroids from solutions, elastomers, and pessaries have been reported [Drug Development and Industrial Pharmacy, Vol. 17, p2269 (1991) and Vol. 11, p 1313 (1985); Pharmaceutical Research, Vol. 6, p848 (1989)]. Peptides and proteins can also be delivered through the vaginal route of administration. Recombinant human relaxin was applied intravaginally as a potential cervical ripening agent [Pharmaceutical Research, Vol. 10, p223 (1993)]. In addition, leutinizing-hormone releasing hormone for induction of ovulation, insulin for control of diabetes, oxytonin for induction of labor, and calcitonin for treatment of osteoporosis have been administered intravaginally with good results [Advanced Drug Delivery Reviews, Vol. 8 , p341 (1992)].

It is another object of this invention to deliver the above referenced drugs through the vaginal route but in a prolonged and a controlled way.

SUMMARY OF THE INVENTION

An object of the present invention is to provide a hydrophilic water swellable but water insoluble vehicle, which incorporates a polystyrene graft copolymer, for intravaginal sustained release of pharmacologically active agents. This vehicle can further be formulated into a user friendly dosage form such as capsules, suppositories, ointments, and films.

A further object of this invention is to provide a pharmaceutical dosage form which gradually hydrates by sorption of tissue fluids at the application site to ultimately a very soft jelly like mass which exhibits adhesion to the mucous surface of the vagina. The resulting hydrogel being very soft and hydrophilic is biocompatible and does not cause adverse local side effects or toxicity.

Another object of the present invention is to provide a vehicle which is at once both convenient to formulate with a pharmacologically active agent and economical to manufacture.

It is still a further object of this invention to provide locally acting pharmaceutical dosage forms for delivery of a spermicide, an antifungal agent, and progesterone and estradiol to the vaginal cavity. In order to accomplish the aforestated objectives, modified formulations based on a graft copolymer of polystyrene with ethylenically unsaturated monomer containing acidic groups , such as acrylic acid or 2-acrylamido-2-methyl-propane sulfonic acid, and optionally containing neutral hydrophilic ethylenically unsaturated monomers such as glyceryl monomethacrylate or N,N-dimethylacrylamide, are described. The compositions of the present invention are obtained by preparing homogeneous mixtures of pharmacologically active agents with the graft copolymer optionally plasticized with polyethylene glycol and/or blended with a compatible water soluble polymer such as poly(N-vinyl 2-pyrrolidone). These formulations can be fabricated into the desired dosage forms by conventional methods.

DETAILED DESCRIPTION OF THE INVENTION

The present invention is directed to a pharmaceutical dosage form, comprising of a polymeric hydrogel forming composition based on graft copolymer, for controlled release of active agents in the vaginal environment. The hydrogel forming pharmaceutical dosage form is comprised of a pharmacologically active agent uniformly dispersed in the graft copolymer, which may be optionally plasticized with a water soluble plasticizer and optionally blended with another compatible water soluble polymer. The graft copolymer suitable for use in this invention has a hydrophilic polymeric main chain and a hydrophobic polymeric side chain (FIG. 1). The main chain is comprised of monomeric units having acidic groups and optionally neutral monomeric units. The preferred hydrophobic side chain moiety is polystyrene. The graft copolymer is prepared by free radical initiated polymerization of a polystyrene macromonomer having an ethylenically unsaturated functional group (FIG. 2) with the acidic and neutral hydrophilic comonomers. The acidic comonomers suitable for preparation of the graft copolymer include: acrylic acid, methacrylic acid, itaconic acid, 2-acrylamido-2-methyl-propane sulfonic acid, and 2-sulfoethyl methacrylate. The neutral comonomers of the main chain include acrylamide, methacrylamide, 2-hydroxyethyl methacrylate, N,N-dimethylacrylamide, polyethylene glycol monomethacrylate, and glyceryl methacrylate. The method of preparation of the graft copolymer for use in this invention is analogous to that for poly(N,N-dimethylacrylamide-g-styrene) as disclosed in R. Milkovich, et al., U.S. Pat. No. 4,085,168, which is incorporated herein by reference.

The monomeric moieties of the graft copolymer are selected to perform the needed functions. The acidic and neutral hydrophilic monomeric units provide the hydrophilicity to absorb aqueous fluids, whereas the polystyrene graft chains contribute to the integrity and water insolubility of the copolymer, thus resulting in a water swollen but insoluble jelly like mass in the biological environment. The acidic functionality of the copolymer in addition contributes to adhesion to the mucous surface of the vagina so as to attain the necessary residence time of the gel. Release of the pharmacological agent from the swollen gel occurs gradually by a process of diffusion. The hydrophilic neutral comonomer contributes to modification of the hydrophilicity and polarity of the graft copolymer for optimizing solubility of the pharmacological agents in it. The relative proportions of the three types of monomers may vary within certain limits. The proportion of polystyrene macromonomer may vary from about 1 to about 20 per cent by weight, typically from 1 to 10 percent by weight, and preferably from 1 to 5 percent by weight, based on the total weight of the copolymer. The ethylenically unsaturated monomer containing acidic groups may vary from 10 to 90 percent by weight of the copolymer. Finally, the neutral hydrophilic monomer may vary from 0 to 89 percent by weight of the copolymer. The principal drug delivery vehicle of the dosage form of the present application is a thermoplastic graft copolymer. The active drug delivery vehicle consists essentially of the thermoplastic graft copolymer, by which is meant that although ingredients such as water, water soluble or water swellable polymers, and adjuvants, such as plasticizer, and diluents, such as solvents can be present, other ingredients that materially alter the basic and novel characteristics of the drug delivery vehicle are absent.

The graft copolymer for use in this invention exhibits microphase separation with a hydrophilic/hydrophobic domain system. The morphology of the graft copolymer is characterized by a hydrophilic continuous phase and a hydrophobic dispersed phase, which prevents the continuous phase from dissolving in water. Thus, when the graft copolymer is placed in an aqueous environment, it absorbs water and swells to an equilibrium volume, but does not dissolve in water. More specifically, the graft copolymer has an equilibrium water content, defined as the percentage by weight of water absorbed, based on the weight of the fully hydrated sample, of greater than 90%, and typically greater than 95%. Such graft copolymers are thermoplastic. Accordingly, they are soluble in conventional organic solvents and soften or melt upon the application of heat. The hydrogel forming graft copolymers are distinguished from thermosetting polymers, such as mucoadhesive hydrogels ["Vaginal and Reproductive System Treatments using a Bioadhesive Polymer", Joseph R. Robinson and William J. Bologna, J. Control. Rel., Vol. 28, p87–94 (1994)], which are insoluble in organic solvents and do not melt upon heating. The graft copolymers for use in the present invention may therefore be prepared separately, purified, and then formulated with the pharmacological agent and other excipients by either solution mixing/casting or melt mixing process. For example, a graft copolymer of N,N-dimethylacrylamide, acrylic acid and polystyrene macromonomer may be prepared by free radical initiated solution polymerization. The starting materials are reacted in the presence of a polymerization solvent, such as ethyl acetate, ethanol, methyl ethyl ketone, acetone, tetrahydrofuran, mixtures thereof and the like, and a polymerization initiator (e.g. azobisisobutyronitrile) at a reaction temperature in the range of up to 80° C. The resulting solution containing the copolymer is then optionally purified to remove unreacted monomer and other impurities. For example, the copolymer solution may be precipitated with a non-solvent, such as diethyl ether, at a weight ratio of about 1:4. The resulting precipitated copolymer is separated, washed with excess non-solvent, and dried. The advantage of this process is that the pharmacological agent is not subject to chemically reactive species during the polymerization process as would be the case for thermosetting polymers.

Blending compatible water soluble polymers with the graft copolymer increases its equilibrium hydration capacity. Compatible water soluble polymers suitable for blending with the graft copolymer include, but are not limited to, poly(N-vinyl 2-pyrrolidone) and poly(N,N-dimethylacrylamide). The proportion of the water soluble polymer used in blending may vary from 0 to 75 percent by weight, based on the combined weights of the water soluble polymer and the graft copolymer.

Polyethylene glycol having a molecular weight of about 300 to 1500, preferably 400 to 600, can be used as a water soluble plasticizer for the graft copolymer to prepare a vaginal drug delivery dosage form. Alternatively, glycerine may also be used as a water soluble plasticizer. The proportion of the water soluble plasticizer in the dosage form may vary from about 10 to 50, preferably 20 to 40, percent by weight of the dosage form.

The hydrogel forming dosage forms of this invention are particularly suitable for the vaginal delivery of, but not limited to, the following pharmacologically active agents.:

Miconazole nitrate and clotrimazole are two suitable antifungal agents for the treatment of vaginal yeast (candida) infection. The concentration of clotrimazole in the dosage form can vary from 1 to 10 percent by weight, based on the total weight of the dosage form. The polymeric hydrogel forming dosage form provides the benefits of sustained release of the dosage form over a prolonged period of time thus increasing the therapeutic effectiveness and patient compliance. The currently marketed products are creams which essentially dump the active agent at the site of application reducing the duration of therapeutic effectiveness. The hydrogel dosage form has an added benefit in that it does not contain some of the inactive ingredients present in the cream products, such as preservatives and surfactants, which may be potentially irritating to body tissues.

Nonoxynol-9, which is one of the major spermicidal agents used in the marketed spermicidal contraceptive products, may be incorporated in to the hydrogel forming dosage form. The concentration of nonoxynol-9 may vary from 10 to 40 percent by weight, based on the total weight of the dosage form. The currently available products are effective for only a short period of time (approximately 1hour). Sustained release of nonoxynol-9 from the hydrogel forming dosage form can provide spermicidal activity for a period of greater than 8 hours. Greatly enhanced user convenience is an important advantage associated with the dosage form of this invention.

Progesterone formulated in the hydrogel forming dosage form can be used for transvaginal administration for the treatment of menopausal disorders (in combination with estrogen replacement therapy), menstrual irregularities, infertility due to inadequate luteal phase, and other disorders associated with progesterone deficiency. The concentration of progesterone may vary from 3 to 15, preferably from 4 to 10 percent by weight, based on the total weight of the dosage form. This dosage form can provide sustained release of progesterone resulting in therapeutic effectiveness for a period of 2 to 7 days. Marketed transvaginal formulations are currently available as cocobutter base suppositories or progesterone gelatin capsules. These formulations have the disadvantages of twice a day administration and local side effects of unacceptable vaginal discharges. Use of the highly biocompatible hydrogel forming progesterone dosage form can alleviate these problems and significantly improve patient convenience and compliance.

Formulation of the pharmacologically active agent with the other components in accordance with this invention can be simply accomplished by dissolving all the components (for example the graft copolymer, water soluble plasticizer, and optionally compatible water soluble polymer) in a suitable solvent, such as acetone, chloroform, tetrahydrofuran, N,N-dimethylformamide, etc. and then isolating the formulated mixture by evaporating the solvent by heating under vacuum. Alternatively, all the components can be homogeneously mixed in the melt in a conventional processing equipment such as an extruder or a sigma blade mixer.

The kinds of sustained release vaginal dosage forms that can be prepared from the formulations of the present invention include, but are not limited to a powder, a film, and a gelatin capsule or a suppository or an ointment containing the powdered polymeric formulation of the pharmacologically active agent. The methods of preparation of such dosage forms are commonly known in the field to those skilled in the art.

EXAMPLE 1

In a 1-liter resin kettle equipped with a stirrer, a thermometer, a condenser, and a nitrogen inlet tube, was placed 47.5 g. of N,N-dimethylacrylamide, 47.5 g. of acrylic acid, and 5.0 g. of polystyrene methacrylate macromonomer having a number average molecular weight of 12,000 (manufactured by Polymer Chemistry Innovations, Inc.), and 170 ml of ethyl acetate. A solution of 100 mg of azobisisobutyronitrile in 5.0 ml of ethyl acetate was slowly added to the mixture under constant stirring until a completely clear solution was obtained. The reaction mixture was heated to 50° C. and maintained at that temperature for a period of 1 hour under nitrogen atmosphere. The reaction mixture was then further heated and allowed to reflux for an additional period of 2 hours also under nitrogen atmosphere, after which time a viscous polymer solution was obtained. The resultant graft copolymer was precipitated by gradual addition of the solution to 1200 ml of diethyl ether under vigorous agitation. The precipitate was isolated by filtration, washed with excess diethyl ether, and dried at 50° C. under vacuum until free of solvent and residual monomer odor to yield 95 g. of the graft copolymer.

EXAMPLE 2

A solution of 10 g. of the graft copolymer, 15 g. of poly(N,N-dimethylacrylamide), 10 g. of polyethylene glycol, and 700 mg of clotrimazole in 200 ml of chloroform was obtained by stirring the mixture for a period of 24 hours. An aliquot of the solution was cast over a silicone coated release paper and dried in an air oven at 50° C. for a period of 2 hours to yield 60 square inches of 4 mil thick soft polymeric film containing 2% clotrimazole. The film upon equilibration in normal saline solution for a period of 24 hours formed a jelly like mass.

EXAMPLE 3

A solution of 10 g. of the graft copolymer, 15 g. of poly(N,N-dimethylacrylamide), 5.0 g. of polyethylene glycol, and 10.0 g of nonoxynol-9 in 200 ml of chloroform was obtained by stirring the mixture for a period of 24 hours. An aliquot of the solution was cast over a silicone coated release paper and dried in an air oven at 50° C. for a period of 2 hours to yield 60 square inches of 4 mil thick soft polymeric film containing 25% nonoxynol-9. The film upon equilibration in normal saline solution for a period of 24 hours formed a jelly like mass.

EXAMPLE 4

A solution of 10 g. of the graft copolymer, 15 g. of poly(N,N-dimethylacrylamide), 10 g. of polyethylene glycol, and 2.1 g. of progesterone in 200 ml of chloroform was obtained by stirring the mixture for a period of 24 hours. An aliquot of the solution was cast over a silicone coated release paper and dried in an air oven at 50° C. for a period of 2 hours to yield 60 square inches of 4 mil thick polymeric film containing 5.7% progesterone. The film upon equilibration in normal saline solution for a period of 24 hours formed a jelly like mass.

What is claimed is:

1. A sustained release vaginal dosage form comprising:
   (A) a drug or a plurality of drugs to be delivered, and
   (B) a drug delivery vehicle consisting essentially of a thermoplastic graft copolymer, said graft copolymer being a reaction product of:
      (1) a polystyrene macromonomer having an ethylenically unsaturated functional group, and
      (2) at least one hydrophilic acidic monomer having an ethylenically unsaturated functional group;
      wherein the weight percent of the polystyrene macromonomer in the graft copolymer is between about 1 and about 20%, and the weight percent of the total hydrophilic monomer in the graft copolymer is between 80 and 99%, wherein at least about 10% of said total hydrophilic monomer is acidic, said graft copolymer when fully hydrated having an equilibrium water content of at least 90%,
   said graft copolymer being present in said dosage form in an amount sufficient to cause said dosage form to form a water swollen but insoluble jelly like mass upon contact with the biological environment.

2. A sustained release vaginal dosage form as in claim 1 where the weight percent of the drug to be delivered is between 0.001 and 40.

3. A sustained release vaginal dosage form as in claim 1 where the hydrophilic monomer further comprises a neutral monomer.

4. A sustained release vaginal dosage form as in claim 1 where the hydrophilic monomer is acrylic acid.

5. A sustained release vaginal dosage form as in claim 3 where the hydrophilic neutral monomer is N,N-dimethylacrylamide.

6. A sustained release vaginal dosage form as in claim 1 in the form of powder.

7. A dispersion comprising a sustained release vaginal dosage form as in claim 1, and any acceptable liquid pharmaceutical excipient.

8. A sustained release vaginal dosage form as in claim 1 as a unit dose insert.

9. A sustained release vaginal dosage form as in claim 1 where the drug is a spermicide.

10. A sustained release vaginal dosage form as in claim 9 where the spermicidal drug is Nonoxynol 9.

11. A sustained release vaginal dosage form as in claim 1 where the drug is a progestin.

12. A sustained release vaginal dosage form as in claim 11 where the drug is progesterol.

13. A sustained release vaginal dosage form as in claim 1 where the drug is an estrogen.

14. A sustained release vaginal dosage form as in claim 13 where the drug is estradiol.

15. A sustained release vaginal dosage form as in claim 13 where the drug is estriol.

16. A sustained release vaginal dosage form as in claim 1 where the drug is an antifungal agent.

17. A sustained release vaginal dosage form as in claim 16 where the drug is miconazole nitrate.

18. A sustained release vaginal dosage form as in claim 16 where the drug is clotrimazole.

19. A sustained release vaginal dosage form as in claim 1 where the drug is a protein.

20. A sustained release vaginal dosage form as in claim 1 where the drug is a peptide.

21. A sustained release vaginal dosage form as in claim 1 where the drug is systemically absorbed and has therapeutic effectiveness in parts of the body other than the vagina.

22. A sustained release vaginal dosage form comprising:
   (A) a drug or a plurality of drugs to be delivered, and
   (B) a drug delivery vehicle consisting essentially of a thermoplastic graft copolymer, said graft copolymer being a reaction product of:
      (1) a polystyrene macromonomer having an ethylenically unsaturated functional group, and
      (2) at least one hydrophilic acidic monomer having an ethylenically unsaturated functional group,
      (3) and a hydrophilic neutral monomer having an ethylenically unsaturated functional group;
      wherein the weight percent of the polystyrene macromonomer in the graft copolymer is between about 1 and about 20%, and the weight percent of the total hydrophilic monomer in the graft copolymer is between 80 and 99%, wherein at least about 10% of said total hydrophilic monomer is acidic, said graft copolymer when fully hydrated having an equilibrium water content of at least 90%,
   said graft copolymer being present in said dosage form in an amount sufficient to cause said dosage form to form a water swollen but insoluble jelly like mass upon contact with the biological envronment.

23. A sustained release vaginal dosage form comprising:
(A) a drug or a plurality of drugs to be delivered, and
(B) a drug delivery vehicle consisting essentially of a thermoplastic graft copolymer, said graft copolymer being a reaction product of:
  (1) a polystyrene macromonomer having an ethylenically unsaturated functional group, and
  (2) at least one hydrophilic acidic monomer having an ethylenically unsaturated functional group,
  (3) and a hydrophilic neutral monomer having an ethylenically unsaturated functional group;
  wherein the weight percent of the polystyrene macromonomer in the graft copolymer is between about 1 and about 20%, and the weight percent of the total hydrophilic monomer in the graft copolymer is between 80 and 99%, wherein at least about 10% of said total hydrophilic monomer is acidic, said graft copolymer when fully hydrated having an equilibrium water content of at least 90%,
(C) a plasticizer
said graft copolymer being present in said dosage form in an amount sufficient to cause said dosage form to form a water swollen but insoluble jelly like mass upon contact with the biological envronment.

24. A sustained release vaginal dosage form as in claim 23 where the plasticizer is polyethylene glycol.

25. A sustained release vaginal dosage form comprising:
(A) a drug or a plurality of drugs to be delivered, and
(B) a drug delivery vehicle consisting essentially of a thermoplastic graft copolymer, said graft copolymer being a reaction product of:
  (1) a polystyrene macromonomer having an ethylenically unsaturated functional group, and
  (2) at least one hydrophilic acidic monomer having an ethylenically unsaturated functional group;
  wherein the weight percent of the polystyrene macromonomer in the graft copolymer is between about 1 and about 20%, and the weight percent of the total hydrophilic monomer in the graft copolymer is between 80 and 99%, wherein at least about 10% of said total hydrophilic monomer is acidic, said graft copolymer when fully hydrated having an equilibrium water content of at least 90%, and
( C) a plasticizer
said graft copolymer being present in said dosage form in an amount sufficient to cause said dosage form to form a water swollen but insoluble jelly like mass upon contact with the biological environment.

26. A sustained release vaginal dosage form as in claim 25 where the plasticizer is polyethylene glycol.

27. A composition comprising the sustained release vaginal dosage form as in claim 1 and at least one compatible hydrophilic polymer.

28. A composition comprising the sustained release vaginal dosage form as in claim 22 plus a compatible hydrophilic polymer.

29. A composition comprising the sustained release vaginal dosage form as in claim 23 plus a compatible hydrophilic polymer.

30. A composition comprising the sustained release vaginal dosage form as in claim 25 and at least one compatible hydrophilic polymer.

31. A sustained release vaginal dosage form comprising:
(A) a drug or a plurality of drugs to be delivered, and
(B) a drug delivery vehicle consisting essentially of a thermoplastic graft copolymer, said graft copolymer being a reaction product of:
  (1) a polystyrene macromonomer having an ethylenically unsaturated functional group, and
  (2) at least one hydrophilic acidic monomer having an ethylenically unsaturated functional group,
  wherein the weight percent of the polystyrene macromonomer in the graft copolymer is between about 1 and about 20%, and the weight percent of the total hydrophilic monomer in the graft copolymer is between 80 and 99%, wherein at least about 10% of said total hydrophilic monomer is acidic, said graft copolymer when fully hydrated having an equilibrium water content of at least 90%,
(C) an adjuvant selected from the group consisting of:
  (1) a plasticizer, or
  (2) a water soluble or water swellable compatible polymer;
said graft copolymer being present in said dosage form in an amount sufficient to cause said dosage form to form a water swollen but insoluble jelly like mass upon contact with the biological environment.

32. A sustained release vaginal dosage form comprising:
(A) a drug or a plurality of drugs to be delivered, and
(B) a drug delivery vehicle consisting essentially of a thermoplastic graft copolymer, said graft copolymer being a reaction product of:
  (1) a polystyrene macromonomer having an ethylenically unsaturated functional group, and
  (2) at least one hydrophilic acidic monomer having an ethylenically unsaturated functional group,
  (3) and a hydrophilic neutral monomer having an ethylenically unsaturated functional group;
  wherein the weight percent of the polystyrene macromonomer in the graft copolymer is between about 1 and about 20%, and the weight percent of the total hydrophilic monomer in the graft copolymer is between 80 and 99%, wherein at least about 10% of said total hydrophilic monomer is acidic, said graft copolymer when fully hydrated having an equilibrium water content of at least 90%, and
(C) an adjuvant selected from the group consisting of:
  (1) a plasticizer, or
  (2) a water soluble or water swellable compatible polymer.
said graft copolymer being present in said dosage form in an amount sufficient to cause said dosage form to form a water swollen but insoluble jelly like mass upon contact with the biological envronment.

\* \* \* \* \*